US012582588B2

(12) United States Patent
Choi

(10) Patent No.: US 12,582,588 B2
(45) Date of Patent: Mar. 24, 2026

(54) SOLID COSMETIC COMPOSITION FOR BLOCKING ULTRAVIOLET RADIATION HAVING WATER RESISTANCE AND CLEANSING PROPERTIES

(71) Applicant: LG HOUSEHOLD & HEALTH CARE LTD., Seoul (KR)

(72) Inventor: Min-Sung Choi, Seoul (KR)

(73) Assignee: LG HOUSEHOLD & HEALTH CARE LTD., Seoul (KR)

( * ) Notice: Subject to any disclaimer, the term of this patent is extended or adjusted under 35 U.S.C. 154(b) by 705 days.

(21) Appl. No.: 18/009,483

(22) PCT Filed: Jan. 21, 2021

(86) PCT No.: PCT/KR2021/000849
§ 371 (c)(1),
(2) Date: Dec. 9, 2022

(87) PCT Pub. No.: WO2021/251581
PCT Pub. Date: Dec. 16, 2021

(65) Prior Publication Data
US 2023/0233428 A1      Jul. 27, 2023

(30) Foreign Application Priority Data

Jun. 9, 2020    (KR) ........................ 10-2020-0069819
Aug. 12, 2020    (KR) ........................ 10-2020-0101070

(51) Int. Cl.
| | |
|---|---|
| *A61K 8/36* | (2006.01) |
| *A61K 8/02* | (2006.01) |
| *A61K 8/31* | (2006.01) |
| *A61K 8/49* | (2006.01) |
| *A61K 8/92* | (2006.01) |
| *A61Q 17/04* | (2006.01) |

(52) U.S. Cl.
CPC ........... *A61K 8/361* (2013.01); *A61K 8/0229* (2013.01); *A61K 8/31* (2013.01); *A61K 8/4966* (2013.01); *A61K 8/92* (2013.01); *A61Q 17/04* (2013.01)

(58) Field of Classification Search
None
See application file for complete search history.

(56) References Cited

U.S. PATENT DOCUMENTS

| | | | | |
|---|---|---|---|---|
| 6,395,301 B1 * | 5/2002 | Cantin | ..................... | A61K 8/26 |
| | | | | D28/78 |
| 2004/0258721 A1 * | 12/2004 | Bauer | ..................... | A61K 8/064 |
| | | | | 424/401 |

FOREIGN PATENT DOCUMENTS

| | | | |
|---|---|---|---|
| JP | 2002-220320 A | 8/2002 | |
| KR | 10-0749893 B1 | 8/2007 | |
| KR | 10-2010-0135537 A | 12/2010 | |
| KR | 10-2013-0048967 A | 5/2013 | |
| KR | 10-2014-0048690 A | 4/2014 | |
| KR | 10-2015-0116772 A | 10/2015 | |
| WO | WO 2007/078062 A1 | 7/2007 | |
| WO | WO 2018/138802 A1 | 8/2018 | |

OTHER PUBLICATIONS

International Search Report (PCT/ISA/210) issued in PCT/KR2021/000849, dated May 21, 2021.
Written Opinion of the International Searching Authority (PCT/ISA/237) issued in PCT/KR2021/000849 dated May 21, 2021.

* cited by examiner

*Primary Examiner* — Nannette Holloman
(74) *Attorney, Agent, or Firm* — Birch, Stewart, Kolasch & Birch, LLP

(57) ABSTRACT

The present invention provides a solid cosmetic composition which contains a UV-blocking agent, a fatty acid, and a wax, has excellent water resistance and/or cleansing properties, and can effectively block ultraviolet radiation. More specifically, a cosmetic composition for blocking ultraviolet radiation according to the present invention has excellent water resistance at low pH, and is converted to having excellent cleansing properties at high pH during the cleansing of skin, and thus can be effectively used.

18 Claims, 2 Drawing Sheets

【Figure 1】
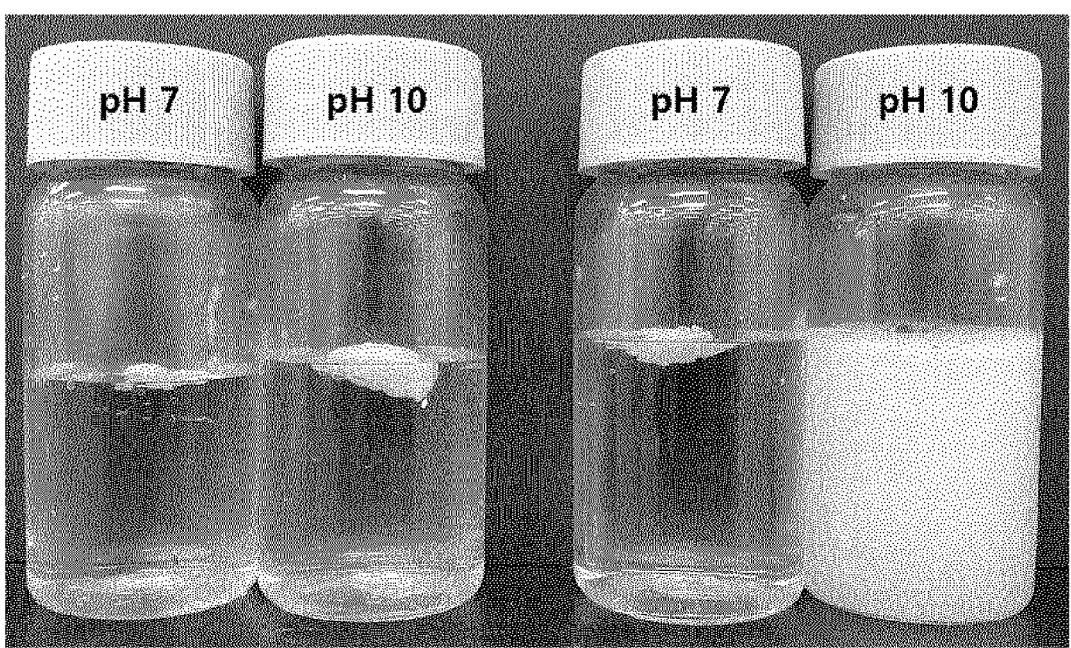
Comparative
Example 1
Example 14
【Figure 2】
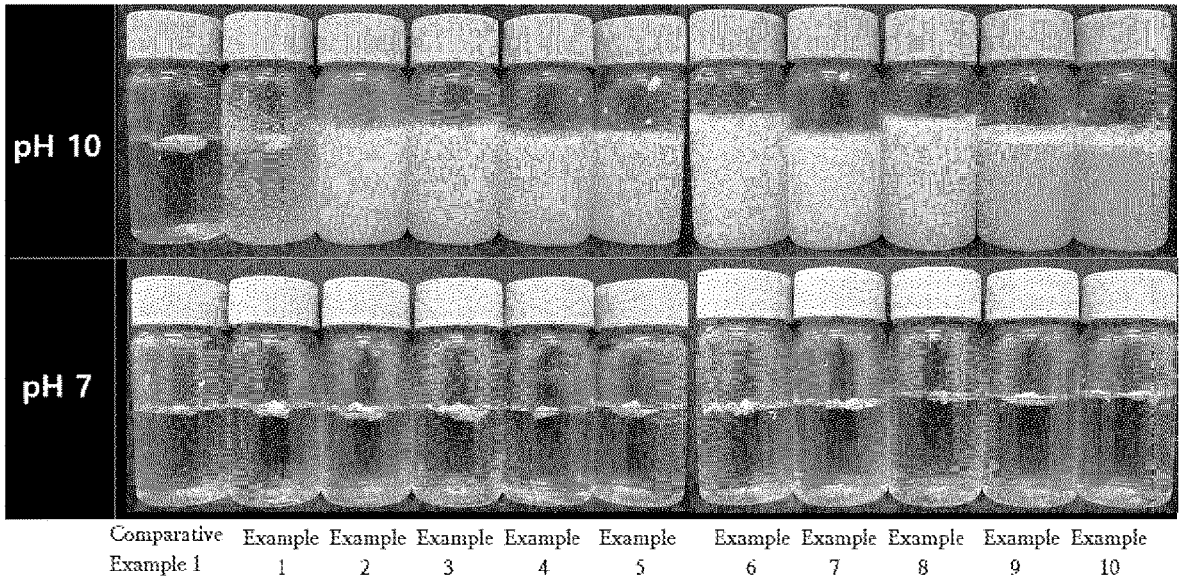

【Figure 3】
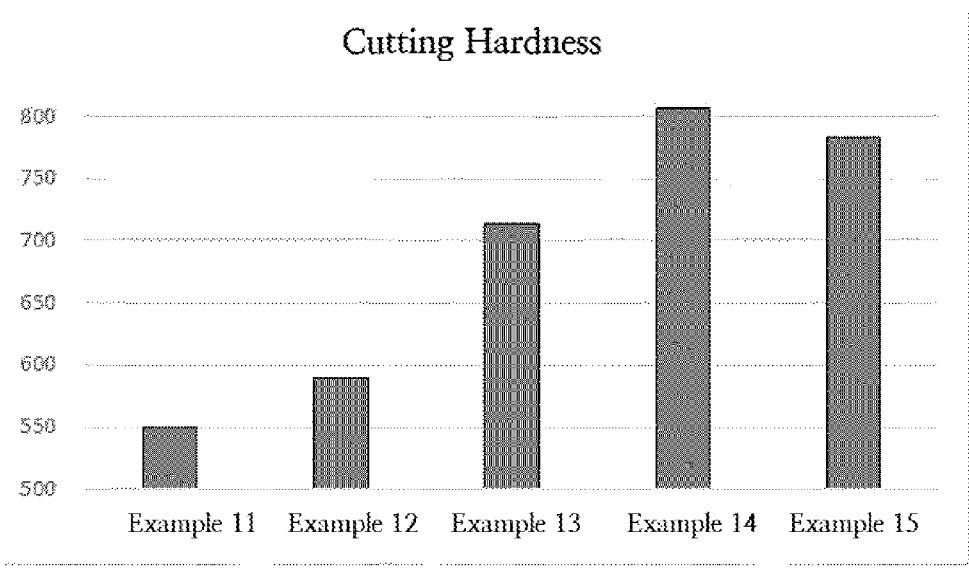
【Figure 4】
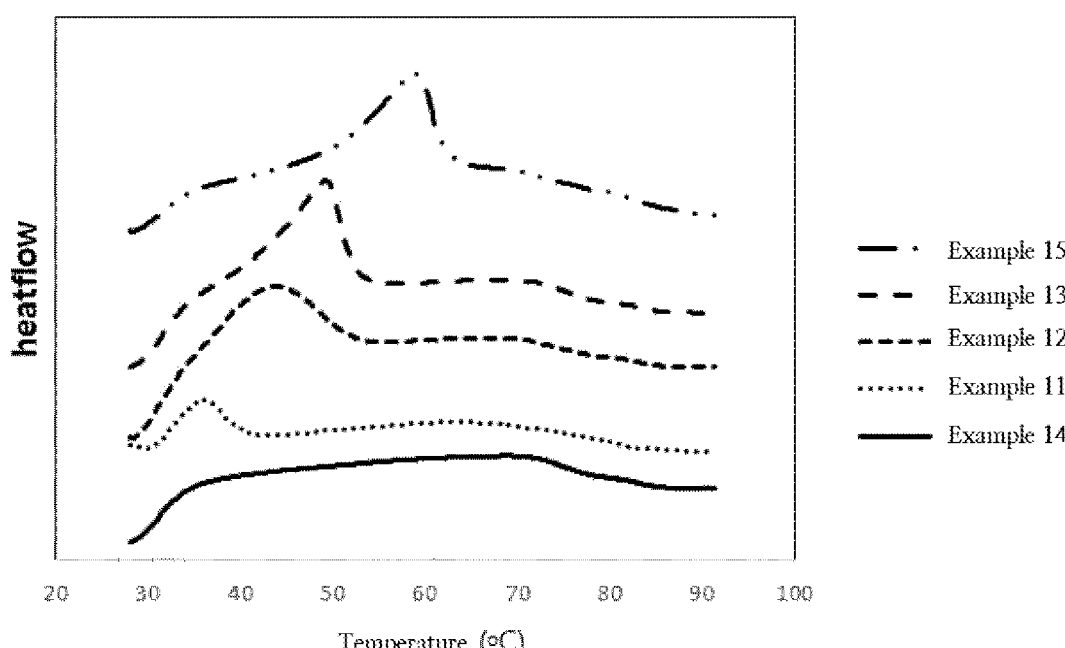

SOLID COSMETIC COMPOSITION FOR BLOCKING ULTRAVIOLET RADIATION HAVING WATER RESISTANCE AND CLEANSING PROPERTIES

TECHNICAL FIELD

This application claims priority to Korean Patent Application No. 10-2020-0069819 filed on Jun. 9, 2020 and Korean Patent Application No. 10-2020-0101070 filed on Aug. 12, 2020, the entire contents of which are incorporated herein by reference.

The present invention relates to a cosmetic composition for blocking ultraviolet radiation. More specifically, it relates to a cosmetic composition for blocking ultraviolet radiation with excellent water resistance and excellent cleansing properties at the same time.

BACKGROUND ART

Water resistance is important for sunscreen cosmetics because sunscreens easily erased by sweat or water cannot sufficiently protect the skin from ultraviolet rays. But at the same time, cleanability is also important. This is because UV-blocking agents that are not completely removed and remain on the skin can give the skin a foreign body sensation and furthermore cause trouble. Therefore, ideal sunscreen cosmetics are not easily erased by water and sweat, but have high cleansing properties and are easily erased when desired.

Meanwhile, stick-type sunscreen cosmetics have recently been developed. The biggest advantage of stick-type sunscreen is that it can be applied without getting cosmetics on one's hands. Ordinary stick-type cosmetics are prepared using oily polymers or wax. When using wax, lip wax or ceresin wax is mainly used.

On the other hand, fatty acids are not practically used in stick-type cosmetics because they are difficult to impart high hardness and high melting point. That is, in order to manufacture conventional solid cosmetics, it is difficult to use substances having a low melting point due to product stability and quality problems. For example, part of the product may melt under high temperature storage conditions, which may change the quality. In addition, there may be a problem of breaking when used due to lowered hardness in the long term. In this respect, fatty acids could not be suitable raw materials for preparing solid cosmetics. Therefore, waxes with higher melting points have been used for the manufacture of solid cosmetics, and even if fatty acids are included, the content thereof is lower than that of other waxes.

As mentioned above, water resistance and ease of washing it off are important factors for sunscreens, but it is difficult to satisfy both at the same time. Furthermore, it is very difficult to satisfy both water resistance and ease of cleansing along with the advantage of ease of use which solid formulations have. There is a need to develop a sunscreen that satisfies all of these three characteristics.

DISCLOSURE

Technical Problem

Therefore, the problem to be solved by the present invention is to provide a cosmetic composition for blocking ultraviolet radiation with excellent water resistance and excellent cleansing properties.

Another problem to be solved by the present invention is to provide a solid cosmetic composition for blocking ultraviolet radiation that is convenient to use and has excellent water resistance and cleansing properties at the same time.

Technical Solution

In order to achieve the above technical problem, the inventors of the present invention have found that solid sunscreen cosmetics containing specific ingredients, particularly high content of fatty acids, are stable and insoluble in general water or sweat with low pH, but easily erased in soapy water with high pH, through which, the present invention was completed.

When a solid sunscreen cosmetic composition containing fatty acids is prepared, water resistance is imparted due to its hydrophobic nature when applied to the skin. However, when exposed to water with a high pH, such as soapy water, the fatty acids undergo a saponification reaction and become having the properties of surfactants, allowing the oily components applied to the skin to be washed away. In order to achieve this purpose, the fatty acid content of the solid cosmetic composition is important.

One embodiment of the present invention provides a cosmetic composition for blocking ultraviolet radiation, comprising UV-blocking agent, fatty acid, oil, and wax, wherein the fatty acid is 5 to 40% by weight based on the total weight of the composition, and is in a solid state.

Oil-in-water emulsions include emulsifiers, and as the emulsifiers re-emulsify the sunscreen on the skin, it is inherently difficult to have water resistance due to the nature of the formulation. In addition, in the case of a water-in-oil emulsions, even if it has water resistance, it forms a competitive relationship with an emulsifier at the interface due to the structural characteristics of fatty acids, so it is difficult to stabilize fatty acids and difficult to include fatty acids in a high content.

On the other hand, in the case of a solid (type) formulation, it can have both water resistance and ease of cleaning, as well as good usability and various advantages as a cosmetic composition.

In the present invention, the object of the present invention may be achieved by appropriately adopting the formulation characteristics of solid phase, the characteristics of fatty acids, and the content of fatty acids.

In one preferred embodiment of the present invention, the composition according to the present invention is substantially free of water.

In the present invention, the term 'substantially free of or do(es) not substantially contain' can be understood to mean containing less than 5% by weight, preferably less than 3% by weight, preferably less than 1% by weight, more preferably less than 0.5% by weight, more preferably less than 0.1% by weight, even more preferably less than 0.01% by weight based on the total weight of the composition, and even if not contained at all (0% by weight) can be included in the scope of the term in the present invention.

Thus, preferably, the composition according to the present disclosure may not contain water at all or contain water in less than 5% by weight, more preferably less than 3% by weight, and even more preferably less than 1% by weight relative to the total weight of the composition.

The cosmetic composition according to the present invention is not dispersed in water of pH 7, but can be dispersed in aqueous solutions of pH 9 to 14.

In the present invention, the term 'dispersion' means that another material is evenly distributed in one material (disperson medium) without sinking to the lower part or floating in the upper part of the dispersion medium. In particular, dispersion in the present specification may mean that a separated phase is not observed after dispersion.

The cosmetic composition according to the present invention is a solid sunscreen cosmetic composition with improved water resistance and cleansing properties.

In one embodiment of the present invention, the wax is contained in 5 to 40% by weight, preferably 6 to 30% by weight, more preferably 12 to 25% by weight, based on the total weight of the composition.

The wax is included to make the solid phase formulation. When the content of the wax is too small, it is difficult to secure the stability of the composition, and when the content of the wax is too large, the composition is too hard, resulting in poor feeling of use or reduced effectiveness of the invention.

In the present invention, the wax includes, but is not limited to, plant-based wax such as candelilla wax, carnauba wax or rice wax; animal waxes such as beeswax or lanolin; mineral waxes such as ozokerite or ceresin wax; petroleum-based waxes such as paraffin wax or microcrystalline wax; and synthetic waxes such as polyethylene wax, polypropylene wax, and ethylene/propylene copolymer.

In the present invention, for example, polyethylene wax having a melting point of 50 to 120° C., preferably 60 to 110° C., and more preferably 70 to 100° C. may be used as the polyethylene wax. In the present invention, as the polyethylene wax, for example, trade name PERFOR-MALENE 400™ of New Phase Technologies may be used.

In the present invention, as the synthetic wax, for example, trade name LIPWAX PZ80-20™ of JAPAN NATURAL PRODUCTS may be used.

In the present invention, the UV-blocking agent may be an inorganic UV-blocking agent and/or an organic UV-blocking agent.

In the present invention, the inorganic UV-blocking agent includes, but is not limited to, titanium oxide, zinc oxide, etc. However, the zinc oxide is less preferred because it may negatively affect the cleansing properties by discharging divalent zinc ions, which interferes with the saponification reaction of fatty acids.

In the present invention, the organic UV-blocking agent includes, but is not limited to, ethylhexyl methoxycinnamate, ethylhexyl salicylate, bis-ethylhexyloxyphenol methoxyphenyltriazine, diethylaminohydroxybenzoylhexylbenzoate, octocrylene, butylmethoxydibenzoylmethane, oxybenzone, octyltriazone, menthylanthranilate, phenylbenzimidazolesulfonic acid, 2-hydroxy-4-methoxybenzophenonesulfonic acid, 3,4-methylbenzylidenecamphor, isoamyl p-methoxycinnamate, homosalate, drometrizoletrisiloxane, benzophenone-3, ethylhexyltriazone, DEA-methoxycinnamate, disodium phenyldiphenzimidazole tetrasulfonate, benzophenone-8, TEA-salicylate, butylmethoxydibenzoylmethane, ethylhexyl dimethyl PABA, etc. These may be used alone or in combination.

Preferably, ethylhexyl methoxycinnamate, octocrylene, ethylhexyl salicylate, bis-ethylhexyloxyphenol methoxyphenyltriazine, diethylaminohydroxybenzoylhexylbenzoate, and the like may be used alone or in combination as the organic UV-blocking agent.

In the present invention, the UV-blocking agent may be contained in 10 to 40% by weight, preferably 15 to 35% by weight, more preferably 18 to 30% by weight, based on the total weight of the composition.

The solid cosmetic composition according to the present invention contains a high content of fatty acids. In the present invention, preferably, the content of the fatty acid may be 5% by weight or more, preferably 10% by weight or more, based on the total weight of the composition. If the content of the fatty acid is less than 5% by weight, the effect of the present invention may be reduced. That is, the solid cosmetic composition of the present invention contains 5 to 40% by weight, preferably 10 to 30% by weight of fatty acids based on the total weight of the composition.

In a preferred embodiment of the present invention, the composition according to the present invention contains the fatty acid in a weight greater than 1 to less than 5 times the weight of the wax.

When determining the content of the fatty acid, it is good to consider the content of the wax together. Because the wax forms a hard film, the ease of cleaning may not be good. In this case, it may be helpful to improve the effect of the invention by prescribing the content of fatty acid more than that of wax.

In the present invention, the fatty acid may be solid or liquid at room temperature, preferably liquid at room temperature. When the fatty acid is liquid at room temperature, it has an effect of improving the hardness of the formulation and has little effect on stability, so that a high content of the fatty acid can be prescribed. However, the effects (ultraviolet ray blocking effect, water resistance, and cleansing properties) of the present invention are all excellent when liquid fatty acids, solid fatty acids, or mixtures thereof are used.

In the present invention, the solid fatty acid at room temperature may be used in a broad sense including a semi-solid state.

In one embodiment of the present invention, when the composition according to the present invention contains solid fatty acids and liquid fatty acids at the same time, the composition according to the present invention contains liquid fatty acids of the fatty acids in an amount greater than 1 to less than 100 times the weight of the solid fatty acids, preferably more than 1 time to less than 50 times in weight, more preferably more than 1 time to less than 20 times in weight, even more preferably more than 1 time to less than 8 times in weight.

When the portion of the liquid fatty acid is more than that of the solid fatty acid, it has various advantages such as improving the sweating (sweating) phenomenon of the formulation.

In the present invention, the fatty acid may be a saturated fatty acid or an unsaturated fatty acid having between 12 and 22 carbon atoms.

Preferably, in the present invention, the fatty acid may be stearic acid, palmitic acid, myristic acid, isostearic acid, behenic acid, or a mixture thereof. More preferably, the fatty acid is isostearic acid. In particular, when the fatty acid is isostearic acid, it is preferable because it less affects the stability and shows excellent effect, and has several advantages such as a feeling of use.

In the present invention, preferably, the degree of neutralization of the fatty acid may be 5 or less, more preferably 1 or less, and most preferably 0 (non-neutralized fatty acid).

In the present invention, the oil contained in the cosmetic composition of the present invention may be a conventional oil used in cosmetic compositions. For example, silicone oil, natural oil, ester oil, hydrocarbon oil, etc. may be used as the oil, but is not limited thereto.

In the present invention, both non-volatile silicone oil and volatile silicone oil can be used as the silicone oil. The non-volatile silicone oil includes, but is limited to, amodimethicone, bisphenylhexamethicone, dimethicone, hexadecylmethicone, methicone, phenyltrimethicone, simethicone, dimethylhydrogensiloxane, stearoxytrimethylsiloxane, and vinyldimethicone and the like. The volatile silicone oil includes, but is limited to, octamethylcyclotetrasiloxane, decamethylcyclopentasiloxane, dodecamethylcyclohexasiloxane, hexamethyldisiloxane, and cyclomethicone and the like.

In the present invention, the natural oil may be an oil obtained from a plant existing in nature. For example, the natural oils include, but are not limited to, sunflower seed oil, avocado oil, orange oil, macadamia seed oil, lemon oil, pine nut oil, jojoba seed oil, olive oil, green tea seed oil, coconut oil, rosehip oil, damask rose flower oil, brazil nut seed oil, drumstick seed oil, grapefruit seed oil, soybean oil, vanilla fruit oil, etc.

In the present invention, the ester-based oil may be an ester compound of a fatty acid and a fatty alcohol. For example, the ester-based oil includes, but is limited to, dipentaerythrityl hexaC$_{5-9}$ acid ester, C$_{12-15}$ alkyl octanoate, myristyl lactate, cetylethylhexanoate, cetyloctanoate, isopropyl myristate, octyldodecyl myristate, hexyl laurate, di(C$_{12-13}$)alkyl maleate, myristyl lactate, octyldodecyl stearoyl stearate, diisostearyl maleate, pentaerythrityl tetraethylhexanoate tri ethylhexanoin, diglyceryl triisostearate, etc.

In the present invention, the hydrocarbon-based oil includes, but is limited to, petroleum-based oils such as liquid paraffin, vaseline, and isoparaffins; synthetic oils such as hydrogenated polydecene, synthetic squalane, and polybutene; and plant-based oils such as vegetable squalane and hydrogenated squalane. Specifically, for example, isohexadecane, isododecane, undecane, squalane (vegetable squalane), synthetic squalane, hydrogenated polydecene alpha olefin oligo, hydrogenated polyisobutene, etc. may be used, but are limited thereto.

Preferably, the oil may be hexyllaurate, triethylhexanoin or a mixture thereof.

In the present invention, the oil may be contained in 5 to 55% by weight, preferably 10 to 50% by weight, more preferably 15 to 40% by weight, and even more preferably 25 to 40% by weight based on the total weight of the composition.

In one embodiment of the present invention, it is preferable that the cosmetic composition according to the present invention does not substantially contain a neutralizing agent.

In the present invention, the cosmetic composition according to the present invention may further includes all kinds of additives that can be used in conventional cosmetics, such as preservatives, fragrances, pigments, powders, thickeners, opacifiers, binders, viscosity modifiers, colorants, flavoring agents, a film-forming agent and the like. These additives can be easily purchased and used commercially.

In the present invention, the solid cosmetic composition according to the present invention may include powder(s) to improve the feeling of use. As the powder, silica, talc, PMMA (polymethylmethacrylate) powder, polymethylsilsesquioxane, etc. may be used, but are not limited thereto. Preferably, the powder is polymethylsilsesquioxane.

In another embodiment of the present invention, the cosmetic composition for blocking a UV according to the present invention contains, relative to the total weight of the composition, 10 to 40% by weight (preferably 15 to 35% by weight, more preferably 18 to 30% by weight) of UV-blocking agent(s) which is ethylhexylmethoxycinnamate, octocrylene, ethylhexyl salicylate, bis-ethylhexyloxyphenolmethoxyphenyltriazine, ethylaminohydroxybenzoylhexylbenzoate, or mixtures thereof; 5 to 40% by weight (preferably, 10 to 30% by weight) of fatty acid(s) which is myristic acid, palmitic acid, stearic acid, isostearic acid, behenic acid, or mixtures thereof; 5 to 40% by weight (preferably 6 to 30% by weight, more preferably 12 to 25% by weight) of wax(s) that is polyethylene, ethylene/propylene copolymer, synthetic wax or a mixture thereof; and 5 to 55% by weight (preferably 10 to 50% by weight, more preferably 15 to 40% by weight, even more preferably 25 to 40% by weight) of oil(s) that is triethylhexanoin, hexylaurate, or a mixture thereof, wherein the composition is solid, and the composition is not dispersed at pH 7 and is dispersed in an aqueous solution of pH 9 to 14.

In the present invention, the composition according to the present invention may further contain 5 to 30% by weight (preferably 7 to 25% by weight, more preferably 9 to 22% by weight) of polymethylsilsesquioxane based on the total weight of the composition.

Preferably, all ingredients described in the present invention do not exceed the maximum limit of use stipulated by relevant laws and regulations of Korea, China, Europe, Japan, etc. (for example, Regulations on the Safety Standards, etc. of Cosmetics (Korea), Safety and Technical Standards for Cosmetics (China), Hygiene Law (China), etc.). That is, preferably, the cosmetic composition according to the present invention contains the ingredients according to the present invention within the content limit permitted by the relevant laws and regulations of each country.

Advantageous Effects

The present invention provides a solid cosmetic composition that has excellent water resistance and cleansing properties at the same time and can effectively block ultraviolet rays. More specifically, the cosmetic composition of the present invention provides a sunscreen composition that has excellent water resistance at a low pH and is converted to have excellent cleansing properties at a high pH when washing the skin.

BRIEF DESCRIPTION OF DRAWINGS

FIG. 1 shows the results of dispersion experiments of Comparative Example 1 and Example 14.

FIG. 2 shows the results of dispersion experiments of Comparative Example 1 and Examples 1 to 10.

FIG. 3 is a graph showing the cutting hardness measurement results of Examples 11 to 15.

FIG. 4 is a graph showing the melting point measurement results of Examples 11 to 15.

MODE FOR INVENTION

Hereinafter, examples and the like will be described in detail to aid understanding of the present invention. However, the examples according to the present invention can be modified in many different forms, and the scope of the present invention should not be construed as being limited to the following examples. Examples of the present invention are provided to more completely explain the present invention to those skilled in the art.

Example 1. Preparation of Comparative Example and Examples According to the Content of Fatty Acids A stick-type sunscreen was prepared according to the prescription shown in Table 1 below. According to the prescription shown in Table 1, all raw materials were mixed, heated to 90° C., mixed well until completely dissolved, and then put in a stick-type container and cooled to room temperature.

TABLE 1

| (Unit: wt %) | Comparative example 1 | Example 1 | Example 2 | Example 3 | Example 4 | Example 5 | Example 6 | Example 7 | Example 8 | Example 9 | Example 10 |
|---|---|---|---|---|---|---|---|---|---|---|---|
| Stearic Acid | | 0.5 | 1.5 | 2.5 | 5 | 7.5 | 10 | 12.5 | 15 | 17.5 | 20 |
| Palmitic Acid | | 0.5 | 1.5 | 2.5 | 5 | 7.5 | 10 | 12.5 | 15 | 17.5 | 20 |
| Hexylaurate | 42 | 41 | 39 | 37 | 32 | 27 | 22 | 17 | 12 | 7 | 2 |
| Polyethylene wax | 15 | 15 | 15 | 15 | 15 | 15 | 15 | 15 | 15 | 15 | 15 |
| Synthetic wax | 2.4 | 2.4 | 2.4 | 2.4 | 2.4 | 2.4 | 2.4 | 2.4 | 2.4 | 2.4 | 2.4 |
| Ethylene/Propylene Copolymer | 0.6 | 0.6 | 0.6 | 0.6 | 0.6 | 0.6 | 0.6 | 0.6 | 0.6 | 0.6 | 0.6 |
| Bis-ethylhexyloxyphe-nolmethoxyphenyltriazine | 2 | 2 | 2 | 2 | 2 | 2 | 2 | 2 | 2 | 2 | 2 |
| Diethylaminohydroxybenzo-ylhexylbenzoate | 2 | 2 | 2 | 2 | 2 | 2 | 2 | 2 | 2 | 2 | 2 |
| Triethylhexanoin | 8 | 8 | 8 | 8 | 8 | 8 | 8 | 8 | 8 | 8 | 8 |
| Ethylhexylmethoxycinnamate | 7 | 7 | 7 | 7 | 7 | 7 | 7 | 7 | 7 | 7 | 7 |
| Ethylhexyl Salicylate | 4 | 4 | 4 | 4 | 4 | 4 | 4 | 4 | 4 | 4 | 4 |
| Octocrylene | 7 | 7 | 7 | 7 | 7 | 7 | 7 | 7 | 7 | 7 | 7 |
| Polymethylsilsesquioxane | 10 | 10 | 10 | 10 | 10 | 10 | 10 | 10 | 10 | 10 | 10 |
| Total | 100 | 100 | 100 | 100 | 100 | 100 | 100 | 100 | 100 | 100 | 100 |

In Table 1, PERFORMALENE 400™, a trade name of New Phase Technologies, was used as the polyethylene wax. LIPWAX PZ80-20™ containing a specific wax and an ethylene/propylene copolymer in a weight ratio of 8:2, a trade name of JAPAN NATURAL PRODUCTS, was used as the synthetic wax and ethylene/propylene copolymer. SESQ-101™ from N&M TECH was used as polymethyl-silsesquioxane. The same ingredients were used in other examples below.

Example 2. Preparation of Examples According to the Type of Fatty Acid

A stick-type sunscreen was prepared according to the prescription shown in Table 2 below. According to the prescription shown in Table 2, all raw materials were mixed, heated to 90° C., mixed well until completely dissolved, and then put in a stick-type container and cooled to room temperature.

TABLE 2

| (Unit: wt %) | Example 11 | Example 12 | Example 13 | Example 14 | Example 15 |
|---|---|---|---|---|---|
| Myristic acid | 15 | | | | |
| Palmitic Acid | | 15 | | | |
| Stearic Acid | | | 15 | | |
| Isostearic Acid | | | | 15 | |
| Behenic Acid | | | | | 15 |
| Hexylaurate | 27 | 27 | 27 | 27 | 27 |
| Polyethylene wax | 15 | 15 | 15 | 15 | 15 |
| Synthetic wax | 2.4 | 2.4 | 2.4 | 2.4 | 2.4 |
| Ethylene/Propylene Copolymer | 0.6 | 0.6 | 0.6 | 0.6 | 0.6 |
| Bis-ethylhexyloxyphenolmethoxyphenyltriazine | 2 | 2 | 2 | 2 | 2 |
| Diethylaminohydroxybenzoylhexylbenzoate | 2 | 2 | 2 | 2 | 2 |
| Triethylhexanoin | 8 | 8 | 8 | 8 | 8 |
| Ethylhexylmethoxycinnamate | 7 | 7 | 7 | 7 | 7 |
| Ethylhexyl Salicylate | 4 | 4 | 4 | 4 | 4 |
| Octocrylene | 7 | 7 | 7 | 7 | 7 |
| Polymethylsilsesquioxane | 10 | 10 | 10 | 10 | 10 |
| Total | 100 | 100 | 100 | 100 | 100 |

Example 3. Preparation of Examples According to the Content of Fatty Acids (Including Samples Wherein Solid Fatty Acids and Liquid Fatty Acids are Used Together)

A stick-type sunscreen was prepared according to the prescription shown in Table 3 below. According to the prescription shown in Table 3, all raw materials were mixed, heated to 90° C., mixed well until completely dissolved, and then cooled to room temperature in a stick-type container.

TABLE 3

| (Unit: wt %) | Example 16 | Example 17 | Example 18 | Example 19 | Example 20 | Example 21 | Example 22 | Comparative example 2 | Comparative example 3 |
|---|---|---|---|---|---|---|---|---|---|
| Palmitic Acid | 8 | 8 | 10 | 10 | — | — | — | 8 | 8 |
| Stearic Acid | 8 | 8 | 10 | 10 | 6 | 3 | — | 8 | 8 |
| Isostearic Acid | 4 | 8 | 4 | 8 | 15 | 18 | 21 | 8 | 8 |
| Hexylaurate | To 100 | To 100 | To 100 | To 100 | To 100 | To 100 | To 100 | To 100 | To 100 |
| Polyethylene wax | 16 | 16 | 16 | 16 | 16 | 16 | 16 | — | 3 |
| Synthetic wax | 2.4 | 2.4 | 2.4 | 2.4 | 2.4 | 2.4 | 2.4 | — | — |
| Ethylene/Propylene Copolymer | 0.6 | 0.6 | 0.6 | 0.6 | 0.6 | 0.6 | 0.6 | — | — |
| Bis-ethylhexyloxyphe-nolmethoxyphenyltriazine | 3 | 3 | 3 | 3 | 3 | 3 | 3 | 3 | 3 |
| Diethylaminohydroxybenzo-ylhexylbenzoate | 2 | 2 | 2 | 2 | 2 | 2 | 2 | 2 | 2 |
| Triethylhexanoin | 8 | 8 | 8 | 8 | 8 | 8 | 8 | 8 | 8 |
| Ethylhexylmethoxycinnamate | 7 | 7 | 7 | 7 | 7 | 7 | 7 | 7 | 7 |
| Ethylhexyl Salicylate | 4 | 4 | 4 | 4 | 4 | 4 | 4 | 4 | 4 |
| Octocrylene | 7 | 7 | 7 | 7 | 7 | 7 | 7 | 7 | 7 |
| Polymethylsilsesquioxane | 20 | 20 | 20 | 20 | 20 | 20 | 20 | 20 | 20 |
| Total | 100 | 100 | 100 | 100 | 100 | 100 | 100 | 100 | 100 |

Experimental Example 1. Evaluation of Dispersion Force (Dispersion Experiment)

The dispersion experiment was conducted by dispersing the solid sun stick in normal water having a pH of 7 and an aqueous solution of tromethamine having a pH of 10 and observing the degree of dispersion (FIG. 1, FIG. 2 and Table 4).

As a result, Comparative Example 1 was not dispersed in all of the aqueous solutions of pH 7 and 10, but all Examples were dispersed. The degree of dispersion was particularly excellent when the fatty acid content was high compared to the wax.

TABLE 4

|  | pH 7 | pH 10 |
|---|---|---|
| Comparative example 1 | X | X |
| Example 1 | X | Δ |
| Example 2 | X | ○ |
| Example 3 | X | ○ |
| Example 4 | X | ○ |
| Example 5 | X | ○ |
| Example 6 | X | ◎ |
| Example 7 | X | ◎ |
| Example 8 | X | ◎ |
| Example 9 | X | ◎ |
| Example 10 | X | ◎ |
| Example 11 | X | ◎ |
| Example 12 | X | ◎ |
| Example 13 | X | ◎ |
| Example 14 | X | ◎ |
| Example 15 | X | ◎ |
| Example 16 | X | ◎ |
| Example 17 | X | ◎ |
| Example 18 | X | ◎ |
| Example 19 | X | ◎ |
| Example 20 | X | ◎ |
| Example 21 | X | ◎ |
| Example 22 | X | ◎ |

X: It was not dispersed at all, and transparent water was observed.
Δ: Slightly dispersed and the water turned slightly cloudy.

○: It is dispersed and the water turns cloudy.

◎: It is dispersed, the water turns cloudy, and a bubble layer is formed.

Experimental Example 2. Evaluation of Water Resistance

A water resistance test was conducted with the sun stick prepared according to the prescription in Table 1 above. After applying the sun stick to the PMMA plate with a thickness of 1.3 mg/cm², it was dried for more than 15 minutes. The transmittance of the dried PMMA plate was measured using a spectrophotometer. The transmittance was measured every 1 nm for the wavelength in the range of 290 to 400 nm at three different positions of the PMMA plate. To evaluate water resistance, a round stainless steel container was properly filled with tap water, and the PMMA plate was fixed so that it was completely submerged in water. After leaving it for 30 minutes while stirring at 3000 rpm using a disper, the PMMA plate was taken out and dried for more than 30 minutes. The transmittance in the wavelength range of 290 to 400 nm was measured using a spectrophotometer again with the completely dried PMMA plate. The transmittance measured before and after immersion was converted into an in-vitro SPF value according to the formula below and compared. The water resistance ratio was calculated by dividing the SPF after immersion by the SPF before immersion. The results are summarized in Table 5 below.

$$SPF = \sum_{290}^{400} E_\lambda S_\lambda / \sum_{290}^{400} E_\lambda S_\lambda T_\lambda$$

$E_\lambda$: Erythemal action spectrum $S_\lambda$: Spectral irradiance (W/m²/nm)

$T_\lambda$: Transmittance

As a result, it was confirmed that the sun sticks of Examples 1 to 10 containing fatty acids had a better water resistance ratio than the sun sticks (Comparative example 1) that did not contain fatty acids. Since fatty acids do not react with water with neutral pH and are hydrophobic, they do not affect the water resistance of the sun stick. Rather, fatty acids reacted with a small amount of divalent ions contained in water to generate insoluble sediment, resulting in better water resistance and a higher SPF after immersion due to the scattering effect of insoluble sediment.

TABLE 5

|  | SPF before immersion | SPF after immersion | Water resistance ratio (%) |
|---|---|---|---|
| Comparative example 1 | 89.45 ± 10.04 | 19.7 ± 7 | 22.02 |
| Example 1 | 77.05 ± 13.46 | 53.75 ± 34.31 | 69.76 |
| Example 2 | 101.75 ± 30.53 | 55.57 ± 48.63 | 54.61 |
| Example 3 | 120.05 ± 27.96 | 92.21 ± 93.4 | 76.81 |
| Example 4 | 112.82 ± 13.78 | 91.25 ± 32.49 | 80.88 |
| Example 5 | 94.98 ± 30.74 | 106.92 ± 104.7 | 112.57 |
| Example 6 | 154.1 ± 56.96 | 291.57 ± 165.83 | 189.21 |
| Example 7 | 47.97 ± 8.01 | 17.79 ± 2.52 | 37.09 |
| Example 8 | 67.58 ± 15.91 | 26.54 ± 5.86 | 39.27 |
| Example 9 | 28.08 ± 2.9 | 37.63 ± 2.28 | 134.01 |
| Example 10 | 35.00 ± 2.29 | 101.58 ± 69.5 | 290.23 |

Experimental Example 3. Detergency Evaluation

The cleaning power was evaluated for the sun stick prepared with the prescription of Table 1 above. After applying each sun stick to a thickness of 1.3 mg/cm$^2$ on a PMMA plate, the transmittance in the 290-400 nm region was measured using a spectrophotometer. The transmittance was measured at three different positions of the PMMA plate. After that, 0.2 g of a 20% dispersion of cleansing foam was placed on the PMMA plate and washed evenly for 20 seconds using an electric cleanser. After rinsing well with lukewarm water, it was completely dried for 30 minutes or more, and the transmittance was measured again using a spectrophotometer. The cleaning rate was calculated by the formula below. At this time, the value that transmits more ultraviolet rays than the control plate was replaced with the value of the control plate, and it was assumed that the cleaning rate is 100%. The results are shown in Table 6 below.

$$\text{Cleaning rate } (\%) = \sum\nolimits_{290}^{400} \frac{T_\lambda^{after} - T_\lambda^{before}}{T_\lambda^{control} - T_\lambda^{before}} \times 100$$

$T_\lambda^{control}$: Transmittance of the control PMMA plate at a single wavelength $T_\lambda^{before}$: Transmittance before cleaning at a single wavelength $T_\lambda^{after}$: Transmittance after cleaning at a single wavelength Examples 1 to 10 showed a higher cleaning rate than Comparative example 1. This is because when fatty acids meet soapy water with a high pH, a saponification reaction occurs which leads to amphoteric properties. Fatty acid not only acts as a surfactant, but also helps the oil film to be washed away by leaving the sunscreen oil film through a saponification reaction.

TABLE 6

|  | Cleaning rate (%) | Improvement rate compared to Comparative example 1 (%) |
|---|---|---|
| Comparative example 1 | 64.56 | — |
| Example 1 | 70.50 | 9.20 |
| Example 2 | 71.76 | 11.15 |
| Example 3 | 80.08 | 24.04 |
| Example 4 | 78.24 | 21.19 |
| Example 5 | 83.62 | 29.52 |
| Example 6 | 79.81 | 23.62 |

TABLE 6-continued

|  | Cleaning rate (%) | Improvement rate compared to Comparative example 1 (%) |
|---|---|---|
| Example 7 | 89.34 | 38.38 |
| Example 8 | 85.88 | 33.02 |
| Example 9 | 83.41 | 29.20 |
| Example 10 | 81.21 | 25.79 |

Experimental Example 4. Hardness and Melting Point and Long-Term Stability Test at High Temperature When a high content of solid fatty acids is included together with wax, stability such as decrease in hardness and melting point may be affected. Therefore, caution is required when using high-content fatty acids in solid-phase formulations. This is expected to be because the fatty acids in the solid phase affect the crystal structure by participating in crystal formation, but the present invention is not limited to this theoretical mechanism.

Experimental Example 4-1. Cutting Hardness Measurement

The cutting hardness was measured and the results are shown in FIG. 3. To measure the cutting hardness, each sample was made into a cylindrical shape with a circular shape and a diameter of about 2.5 cm. It was measured using an applicator #30 equipped with a piano string at a speed of 2 cm/min at a depth of 1.5 cm using a durometer.

As a result, the hardness of Example 14 using isostearic acid, which is liquid at room temperature, was the highest. This is expected to be because the solid fatty acid affected the crystal structure of the wax, whereas the liquid fatty acid did not affect the crystal structure, but the present invention is not limited to this theoretical mechanism.

Experimental Example 4-2. Melting Point Measurement

The melting point according to the type of fatty acid was observed using DSC. DSC was observed while increasing the temperature by 10° C. per minute from 30° C. to 95° C. FIG. 4 shows the melting point measurement results.

As a result, it was found that when solid fatty acids were used, the melting point of solid formulations was lowered due to the melting point inherent in fatty acids. However, when liquid fatty acids were used, there was no phenomenon of lowering the melting point. This is expected because solid fatty acids participate in crystal formation and affect the crystal structure, whereas liquid fatty acids do not participate in crystal formation and do not affect the crystal structure. However, the present invention is not limited to this theoretical mechanism.

Experimental Example 4-3. High-Temperature Long-Term Stability Test

A stability test was conducted using the prepared sun stick. The experimental results are shown in Table 7 and Table 8 below.

As a result, Examples 11 and 12, which had a low melting point, did not maintain their original hardness at high temperatures, and showed a tendency to decrease their hardness when they were in high temperature conditions for a long period of more than one month.

Sweating is an important stability factor in solid oil-wax gel formulations. Sweating was observed when a high content of solid fatty acids was used, but no sweating was observed when liquid fatty acids were used.

TABLE 7

| | Type of fatty acid | 40° C. Stability | 45° C. Stability | 50° C. Stability | Sweating Stability |
|---|---|---|---|---|---|
| Example 11 | Myristic acid | Δ | X | X | X |
| Example 12 | Palmitic Acid | Δ | Δ | X | X |
| Example 13 | Stearic Acid | ○ | ○ | ○ | X |
| Example 14 | Isostearic Acid | ○ | ○ | ○ | ○ |
| Example 15 | Behenic Acid | ○ | ○ | ○ | Δ |

(In Table 7, ○ means excellent stability, Δ means moderate stability, and X means poor stability.)

When solid fatty acids and liquid fatty acids were used together, sweating occurred when the content of liquid fatty acids was lower than that of solid fatty acids, as in Examples 16-19. On the other hand, as in Examples 20-22, it was confirmed that the sweating phenomenon was improved when the content of liquid fatty acid was higher. In addition, even if it contains solid fatty acids, as in Comparative Examples 2 and 3, if wax is not included or the wax content is low, the stick-type sunscreen is too soft, so it is not suitable as a solid cosmetic, and the stability over time at high temperature was not good.

TABLE 8

| | Solid fatty acid (Unit: wt %) | Liquid fatty acid (Unit: wt %) | Wax content (Unit: wt %) | 40° C. Stability | 45° C. Stability | 50° C. Stability | Sweating Stability |
|---|---|---|---|---|---|---|---|
| Example 16 | 16 | 4 | 19 | ○ | ○ | Δ | X |
| Example 17 | 16 | 8 | 19 | ○ | ○ | Δ | X |
| Example 18 | 20 | 4 | 19 | ○ | ○ | Δ | X |
| Example 19 | 20 | 8 | 19 | ○ | ○ | Δ | X |
| Example 20 | 6 | 15 | 19 | ○ | ○ | ○ | ○ |
| Example 21 | 3 | 18 | 19 | ○ | ○ | ○ | ○ |
| Example 22 | — | 21 | 19 | ○ | ○ | ○ | ○ |
| Comparative example 2 | 16 | 8 | 0 | X | X | X | X |
| Comparative example 3 | 16 | 8 | 3 | X | X | X | X |

(In Table 8, ○ means excellent stability, Δ means moderate stability, and X means poor stability)

Experimental Example 5. Evaluation of Water Resistance and Detergency

Stick-type sunscreens with the contents shown in Table 2 were prepared and evaluated in the same manner as above. Their water resistance evaluation and detergency evaluation are shown in Table 9 below. As a result, it showed high water resistance ratio and cleaning rate for all types of fatty acids.

TABLE 9

| | SPF before immersion | SPF after immersion | Water resistance ratio (%) | Cleaning rate (%) |
|---|---|---|---|---|
| Example 11 | 127.47 ± 32.16 | 305.68 ± 55.43 | 239.80 | 80.09 |
| Example 12 | 92.21 ± 18.89 | 112.94 ± 35.63 | 122.48 | 77.75 |
| Example 13 | 58.91 ± 13.64 | 163.91 ± 9.98 | 278.23 | 82.04 |
| Example 14 | 127.41 ± 23.59 | 85.04 ± 20.72 | 66.74 | 82.8 |
| Example 15 | 69.08 ± 4.54 | 61.06 ± 43.79 | 88.39 | 80.65 |

The invention claimed is:

1. A cosmetic composition for blocking ultraviolet radiation comprising a UV-blocking agent, a fatty acid, an oil, and a wax, wherein the fatty acid comprises isostearic acid in an amount of 15 to 40% by weight based on the total weight of the composition, and the composition is solid.

2. The cosmetic composition according to claim 1, wherein the composition does not substantially contain water.

3. The cosmetic composition according to claim 1, wherein the wax is 5 to 40% by weight based on the total weight of the composition.

4. The cosmetic composition according to claim 1, wherein the fatty acid is comprised in a weight greater than 1 to less than 5 times the weight of the wax.

5. The cosmetic composition according to claim 1, wherein the fatty acid comprises a liquid fatty acid component, and a solid fatty acid component, and further wherein the liquid fatty acid component is comprised in a weight greater than 1 to less than 100 times the weight of the solid fatty acid component.

6. The cosmetic composition according to claim 1, wherein the UV-blocking agent is 10 to 40% by weight based on the total weight of the composition.

7. The cosmetic composition according to claim 1, wherein the oil is 5 to 55% by weight based on the total weight of the composition.

8. The cosmetic composition according to claim 1, comprising based on the total weight of the composition, 10 to 40% by weight of UV-blocking agent which is ethylhexylmethoxycinnamate, octocrylene, ethylhexylsalicylate, bis-ethylhexyloxyphenolmethoxyphenyltriazine, diethylaminohydroxybenzoylhexylbenzoate, or mixtures thereof;

15 to 40% by weight of fatty acid which is isostearic acid;

5 to 40% by weight of wax which is polyethylene, ethylene/propylene copolymer, synthetic wax, or a mixture thereof;

5 to 55% by weight of oil which is triethylhexanoin, hexyllaurate, or a mixture thereof; and optionally 5 to 30% by weight of polymethylsilsesquioxane, wherein the composition is solid, and the composition is not dispersed at pH 7 and dispersed in an aqueous solution of pH 9 to 14.

9. A method of blocking ultraviolet radiation in a subject while attaining water resistance and cleansing properties, comprising:

applying a stick type cosmetic composition for blocking ultraviolet radiation to skin of the subject,
wherein the stick type cosmetic composition comprises a UV-blocking agent, a fatty acid, an oil, and a wax, and
wherein the fatty acid comprises isostearic acid in an amount of 15 to 40% by weight based on a total weight of the stick type cosmetic composition.

10. The method according to claim 9, wherein the stick type cosmetic composition does not substantially contain water.

11. The method according to claim 9, wherein the wax is 5 to 40% by weight based on the total weight of the stick type cosmetic composition.

12. The method according to claim 9, wherein the fatty acid is comprised in a weight greater than 1 to less than 5 times the weight of the wax in the stick type cosmetic composition.

13. The method according to claim 9, wherein the fatty acid comprises a liquid fatty acid component, and a solid fatty acid component, and further wherein the liquid fatty acid component is comprised in a weight greater than 1 to less than 100 times the weight of the solid fatty acid component in the stick type cosmetic composition.

14. The method according to claim 9, wherein the UV-blocking agent is 10 to 40% by weight based on the total weight of the stick type cosmetic composition.

15. The method according to claim 9, wherein the oil is 5 to 55% by weight based on the total weight of the stick type cosmetic composition.

16. The method according to claim 9, wherein the stick type cosmetic composition comprises, based on the total weight of the stick type cosmetic composition, 10 to 40% by weight of UV-blocking agent which is ethylhexylmethoxycinnamate, octocrylene, ethylhexyl-salicylate, bis-ethylhexyloxyphenolmethoxyphenyltri-azine, diethylaminohydroxybenzoylhexylbenzoate, or mixtures thereof;

15 to 40% by weight of fatty acid which is isostearic acid;

to 40% by weight of wax which is polyethylene, ethylene/propylene copolymer, synthetic wax, or a mixture thereof;

5 to 55% by weight of oil which is triethylhexanoin, hexyllaurate, or a mixture thereof; and optionally 5 to 30% by weight of polymethylsilsesquioxane, wherein the composition is solid, and the composition is not dispersed at pH 7 and dispersed in an aqueous solution of pH 9 to 14.

17. The cosmetic composition according to claim 1, comprising based on the total weight of the composition, 15 to 35% by weight of UV-blocking agent comprising ethylhexylmethoxycinnamate, octocrylene, ethylhexyl-salicylate, bis-ethylhexyloxyphenolmethoxyphenyltri-azine, diethylaminohyd roxybenzoylhexylbenzoate, or mixtures thereof;

15 to 40% by weight of fatty acid comprising isostearic acid;

6 to 30% by weight of wax comprising polyethylene, ethylene/propylene copolymer, synthetic wax, or a mixture thereof;

to 50% by weight of oil comprising triethylhexanoin, hexyllaurate, or a mixture thereof; wherein the composition does not comprise a solid fatty acid, or when it comprises a solid fatty acid, the content thereof is less than that of a liquid fatty acid, wherein the composition does not comprise water, or comprises less than 1% by weight of water based on the total weight of the composition, and wherein the composition is solid.

18. The method according to claim 9, wherein the stick type cosmetic composition comprises, based on the total weight of the stick type cosmetic composition, 15 to 35% by weight of UV-blocking agent comprising ethylhexylmethoxycinnamate, octocrylene, ethylhexyl-salicylate, bis-ethylhexyloxyphenolmethoxyphenyltri-azine, diethylaminohydroxybenzoylhexylbenzoate, or mixtures thereof;

15 to 40% by weight of fatty acid comprising isostearic acid;

6 to 30% by weight of wax comprising polyethylene, ethylene/propylene copolymer, synthetic wax, or a mixture thereof;

10 to 50% by weight of oil comprising triethylhexanoin, hexyllaurate, or a mixture thereof; wherein the composition does not comprise a solid fatty acid, or when it comprises a solid fatty acid, the content thereof is less than that of a liquid fatty acid, wherein the composition does not comprise water, or comprises less than 1% by weight of water based on the total weight of the composition, and wherein the composition is solid.

* * * * *